United States Patent
Bai et al.

(10) Patent No.: US 9,460,491 B2
(45) Date of Patent: Oct. 4, 2016

(54) METHOD FOR BINARY TO CONTONE CONVERSION WITH NON-SOLID EDGE DETECTION

(75) Inventors: Yingjun Bai, San Jose, CA (US); Xing Li, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 1677 days.

(21) Appl. No.: 12/197,348

(22) Filed: Aug. 25, 2008

(65) Prior Publication Data

US 2010/0046856 A1  Feb. 25, 2010

(51) Int. Cl.
| | | |
|---|---|---|
| *G06T 5/00* | (2006.01) | |
| *H04N 1/409* | (2006.01) | |
| *H04N 1/58* | (2006.01) | |
| *G06T 5/20* | (2006.01) | |
| *G01N 21/89* | (2006.01) | |

(52) U.S. Cl.
CPC ............... *G06T 5/002* (2013.01); *G06T 5/20* (2013.01); *H04N 1/409* (2013.01); *H04N 1/58* (2013.01); *G01N 2021/891* (2013.01); *G06T 2207/20012* (2013.01); *G06T 2207/20192* (2013.01)

(58) Field of Classification Search
CPC ......... G06T 5/002; G06T 5/003; G06T 5/20; G06T 2207/20012; G06T 2207/20192; G01N 2021/891; H04N 1/00748; H04N 1/409; H04N 1/4092; H04N 1/58
USPC ....... 382/173, 299, 300, 261; 358/3.27, 536, 358/1.9, 3.26
See application file for complete search history.

(56) References Cited

U.S. PATENT DOCUMENTS

| | | |
|---|---|---|
| 4,958,236 A | 9/1990 | Nagashima et al. |
| 5,008,950 A | 4/1991 | Katayama et al. |
| 5,065,255 A | 11/1991 | Kimura et al. |

(Continued)

FOREIGN PATENT DOCUMENTS

| | | |
|---|---|---|
| EP | 1583064 | 10/2005 |
| EP | 1601184 | 11/2005 |

(Continued)

OTHER PUBLICATIONS

An unofficial copy of the File History as of Oct. 5, 2010 for U.S. Pat. No. 7,773,254 (U.S. Appl. No. 11/272,182).

(Continued)

*Primary Examiner* — Manav Seth
(74) *Attorney, Agent, or Firm* — Michael J. Nickerson; Basch & Nickerson LLP

(57) ABSTRACT

A system and method convert a pixel of binary image data to a pixel of contone image data by determining if a predetermined pixel of binary image data is part of a solid edge or part of a fuzzy edge. A binary to contone conversion circuit converts the predetermined pixel of binary image data to a pixel of a first contone image data value, and a filter circuit converts the predetermined pixel of binary image data to a pixel of a second contone image data value. The filter circuit uses an adaptive filtering operation wherein the adaptive filtering operation utilizes one of a plurality of sets of weighting coefficients to change a characteristic of the filtering operation. The set of weighting coefficients used in the filtering operation are selected in response to a fuzzy edge detection. A selection between the first contone image data value and the second contone image data value is made based upon the determination as whether the predetermined pixel of binary image data is part of a solid edge.

1 Claim, 14 Drawing Sheets

(56) References Cited

U.S. PATENT DOCUMENTS

| | | | |
|---|---|---|---|
| 5,293,430 | A | 3/1994 | Shiau et al. |
| 5,323,232 | A | 6/1994 | Otaka et al. |
| 5,347,599 | A | 9/1994 | Yamashita et al. |
| 5,572,606 | A | 11/1996 | Tanioka |
| 5,617,216 | A | 4/1997 | Wada |
| 5,617,459 | A | 4/1997 | Makram-Ebeid et al. |
| 5,754,710 | A | 5/1998 | Sekine et al. |
| 5,805,724 | A * | 9/1998 | Metcalfe ............ H04N 1/4053 358/3.05 |
| 5,818,964 | A | 10/1998 | Itoh |
| 5,850,474 | A | 12/1998 | Fan et al. |
| 5,898,821 | A * | 4/1999 | Brandkamp ........... G06K 15/02 358/3.06 |
| 5,959,290 | A | 9/1999 | Schweid et al. |
| 6,020,979 | A | 2/2000 | Zeck et al. |
| 6,097,503 | A * | 8/2000 | Felleman ........... H04N 1/40075 358/1.1 |
| 6,130,966 | A * | 10/2000 | Sekine et al. ............. 382/299 |
| 6,181,829 | B1 * | 1/2001 | Clark ............... H04N 1/40062 382/224 |
| 6,229,578 | B1 | 5/2001 | Acharya et al. |
| 6,240,205 | B1 | 5/2001 | Fan et al. |
| 6,259,823 | B1 | 7/2001 | Lee et al. |
| 6,275,303 | B1 | 8/2001 | Fukaya |
| 6,282,325 | B1 | 8/2001 | Han |
| 6,285,464 | B1 | 9/2001 | Katayama et al. |
| 6,343,159 | B1 | 1/2002 | Cuciurean-Zapan et al. |
| 6,427,030 | B1 | 7/2002 | Williams et al. |
| 6,477,282 | B1 | 11/2002 | Ohtsuki et al. |
| 6,594,401 | B1 | 7/2003 | Metcalfe et al. |
| 6,606,420 | B1 | 8/2003 | Loce et al. |
| 6,608,701 | B1 | 8/2003 | Loce et al. |
| 6,683,702 | B1 | 1/2004 | Loce et al. |
| 6,771,832 | B1 | 8/2004 | Naito et al. |
| 6,873,437 | B1 | 3/2005 | Kuwahara et al. |
| 6,920,252 | B2 | 7/2005 | Rouvellou |
| 6,975,434 | B1 | 12/2005 | Pilu et al. |
| 7,039,232 | B2 | 5/2006 | Nagarajan |
| 7,043,080 | B1 | 5/2006 | Dolan |
| 7,079,289 | B2 | 7/2006 | Loce et al. |
| 7,352,490 | B1 * | 4/2008 | Tse ..................... H04N 1/3871 358/1.9 |
| 7,372,992 | B2 | 5/2008 | Ohshita |
| 7,440,139 | B2 | 10/2008 | Loce et al. |
| 7,460,272 | B2 * | 12/2008 | Hara ..................... H04N 1/405 358/1.9 |
| 7,460,276 | B2 | 12/2008 | Xu et al. |
| 7,580,569 | B2 | 8/2009 | Tse et al. |
| 7,773,254 | B2 | 8/2010 | Nagarajan et al. |
| 7,787,703 | B2 * | 8/2010 | McCandlish ......... G06T 7/0083 358/2.1 |
| 7,869,093 | B2 | 1/2011 | Tse et al. |
| 8,023,150 | B2 | 9/2011 | Nagarajan et al. |
| 2002/0126912 | A1 | 9/2002 | Rouvellou |
| 2002/0140983 | A1 | 10/2002 | Shimizu |
| 2002/0159096 | A1 | 10/2002 | Sun et al. |
| 2002/0181797 | A1 | 12/2002 | Young |
| 2002/0191857 | A1 | 12/2002 | Macy |
| 2002/0196467 | A1 | 12/2002 | Delhoune et al. |
| 2003/0007687 | A1 | 1/2003 | Nesterov et al. |
| 2003/0043210 | A1 | 3/2003 | Hanks |
| 2003/0090729 | A1 | 5/2003 | Loce et al. |
| 2003/0091222 | A1 | 5/2003 | Young et al. |
| 2003/0133610 | A1 | 7/2003 | Nagarajan |
| 2003/0193680 | A1 | 10/2003 | Karidi |
| 2004/0066538 | A1 | 4/2004 | Rozzi |
| 2004/0114814 | A1 | 6/2004 | Boliek et al. |
| 2004/0175037 | A1 | 9/2004 | Guleryuz |
| 2005/0163374 | A1 | 7/2005 | Ferman et al. |
| 2005/0206948 | A1 | 9/2005 | Uejo |
| 2005/0259886 | A1 | 11/2005 | Shan |
| 2005/0270582 | A1 | 12/2005 | Hara |
| 2006/0077489 | A1 | 4/2006 | Zhang et al. |
| 2006/0115182 | A1 | 6/2006 | Deng et al. |
| 2006/0132847 | A1 | 6/2006 | Xu et al. |
| 2006/0132850 | A1 | 6/2006 | Banton et al. |
| 2006/0232798 | A1 | 10/2006 | Xu et al. |
| 2006/0257045 | A1 * | 11/2006 | McCandlish ......... G06T 7/0083 382/261 |
| 2007/0053003 | A1 | 3/2007 | Loce et al. |
| 2007/0103731 | A1 | 5/2007 | Tse et al. |
| 2007/0109602 | A1 | 5/2007 | Tse |
| 2007/0172148 | A1 | 7/2007 | Hawley |
| 2007/0172149 | A1 | 7/2007 | Cuciurean-Zapan |
| 2007/0258101 | A1 | 11/2007 | Nagarajan et al. |
| 2008/0049238 | A1 | 2/2008 | Nagarajan et al. |
| 2010/0157374 | A1 | 6/2010 | Nagarajan et al. |
| 2010/0232706 | A1 * | 9/2010 | Forutanpour ................. 382/199 |

FOREIGN PATENT DOCUMENTS

| | | |
|---|---|---|
| GB | 2291308 | 1/1996 |
| JP | 09051431 | 2/1997 |
| WO | WO9930547 | 6/1999 |

OTHER PUBLICATIONS

An unofficial copy of the File History for as of Aug. 16, 2010 U.S. Pat. No. 7,580,569 (U.S. Appl. No. 11/268,147).

An unofficial copy of the Prosecution History as of Aug. 16, 2010 for U.S. Appl. No. 11/126,970.

An unofficial copy of the Prosecution History as of Oct. 5, 2010 for U.S. Appl. No. 11/281,267.

An unofficial copy of the Prosecution History as of Oct. 7, 2010 for U.S. Appl. No. 11/467,584.

An Unofficial copy of the Prosecution History as of Oct. 5, 2010 for U.S. Appl. No. 12/719,233.

An Unofficial copy of the File History as of Oct. 7, 2010 for U.S. Pat. No. 7,352,490 (U.S. Appl. No. 11/531,572).

He, Z.; Chang, T.; Allebach, J.; Bouman C.; Boundary Stitching Algorithm for Parallel Implementation of Error Diffusion; Xerox Corporation, provided Nov. 8, 2008, 12 pages.

Aghdasi, Farzin; Ward, Rahab K.; Reduction of Boundary Artifacts in Image Restoration, IEEE Transactions on Image Processing, vol. 5, No. 4, Apr. 1996, pp. 611-618.

A Machine Translation of Japanese patent publication JP09-051431 cited in a Japanese Office Action dated Nov. 30, 2009 for JPA 2006-128283, Japanese counterpart application of U.S. Appl. No. 11/126,970, JP09-051431 published Feb. 1997.

Unofficial European Search Report dated Feb. 25, 2009 for European Patent Application 06113615.6. (Corresponding to U.S. Appl. No. 11/126,970).

Unofficial European Office Action Dated Oct. 15, 2009 for European Patent Application EP06113615.6 (Corresponding to U.S. Appl. No. 11/126,970).

U.S. Appl. No. 12/719,233—An Unofficial Copy of the Prosecution History Between Oct. 6, 2010 and Jan. 31, 2012 for U.S. Pat. No. 8,023,150 Issued Sep. 20, 2011; U.S. Appl. No. 12/719,233, filed Mar. 8, 2010, Published Jun. 24, 2010, as US-2010-0157374-A1; Inventor: Ramesh Nagarajan et al.

U.S. Appl. No. 11/281,267—An Unofficial Copy of the Prosecution History Between Oct. 6, 2010 and Jan. 31, 2012 and of U.S. Pat. No. 7,869,093 Issued Jan. 11, 2011; U.S. Appl. No. 11/281,267, filed Nov. 17, 2005, Published May 17, 2007, as US-2007-0109602-A1; Inventor: Francis Kapo Tse et al.

* cited by examiner

METHOD FOR BINARY TO CONTONE CONVERSION WITH NON-SOLID EDGE DETECTION

BACKGROUND AND SUMMARY

Digital multifunction reprographic systems are now well known and have replaced optical reprographic systems as a way to reproduce images. In these conventional digital multifunction reprographic systems, a scanner accepts a document to be copied and converts the document into electronic image(s). These images, usually in the form of pages, are then passed to a central control unit which may re-order or reorganize these pages and then, depending on the request of the user of the device, send the pages or images to a destination. Often this destination is an attached printing unit which makes one or more copies of the original document.

However, these conventional devices perform many other functions besides simple copying. The central control unit is usually equipped with a combination of hardware and software elements that enable it to accept input from other sources. The other sources may include some sort of network interface and/or an interface to a telephone system to enable FAX input.

The network interface is usually configured so that it can accept jobs to be printed from any computer source that is connected to the network. This configuration normally includes elements that can convert input documents formatted in one or more page description languages (PDLs) to the native format of the printing device.

An important inner component of such a conventional multifunction digital device is the image path. This is the combination of software and hardware elements that accepts the electronic images from the multiplicity of sources and performs any operations needed to convert the images to the format desired for the various output paths. The image path is usually one of the more complex and costly components of such digital multifunction devices.

The image path for a conventional multifunction device usually has several constraints. One the hand, there is a desire to make the image path utilize data in a multi-bit per pixel format so as to provide for maximum image quality and a minimum loss of critical information in the transformation of documents from paper to electronic form. On the other hand, there are cost constraints and perhaps performance limits on the devices or software that comprise the image path.

Conventional image path electronics may also utilize binary image paths. In this situation, if the input information is scanned in a binary manner at sufficiently high resolution, the scanned image can be reconstructed at the output with little or no perceptible loss of image quality.

Another component of many conventional multifunction devices, especially for those devices having a printing engine that is capable of producing colored output, is the use of analog modulation schemes for the output. In these devices, analog data, in the form of multi-bit pixels, is presented to the modulator of the output printing device. The modulator compares the analog equivalent of the input byte of data to a periodic saw tooth wave. The output therefrom is a signal to the laser imaging component that is pulsewidth modulated by the data stream.

One recent development for conventional multifunction reprographic machines is the use of both binary and analog data in the image path. In such a hybrid image path, the data from the scanner is digitized and converted to binary. All of the intermediate elements of the image path are designed to work with the compact binary data format. Only at the output is the data converted to multi-bit analog form.

One way to implement the resolution conversion is to pass the binary data through the digital equivalent of a two-dimensional low pass filter. The low pass filter may replace each pixel in the binary image by the average of the values within some window centered on the pixel of interest. While such a system does an adequate job of converting the high resolution binary data to analog data, these solutions also have the deleterious effect of smearing sharp edges in the original document. Such an effect is particularly detrimental when reproducing text and line art.

A desirable modification to hybrid image paths would be a design wherein the conversion from binary format to analog format could take into account the existence of sharp edges in the image. Ideally such a scheme would be adaptive, that is, it would change its behavior so that it would apply a resolution conversion scheme appropriate to sharpen edges for those parts of the image that have such edges, but use a different scheme that was better adapted to more continuous tone parts of the image.

Systems that implement resolution conversion schemes similar to that outlined above show significant improvement in image quality compared to those that do not. However, such systems are subject to problems of their own. One such problem is the need to somehow distinguish those parts of the image that have edges from those that do not. Various schemes have been proposed to identify such regions and to develop an image parallel to that being reproduced, a tag image, that identifies those parts of the image that are edges.

All of the above processes deal with the copying process wherein a physical original is presented to the system and the scanner part of the system performs some processing on the digital image of the scanned original to generate the tag information. However, modern multifunction systems are also expected to function as digital printers, accepting input, usually in the form of a page description language format of the document to be printed. There is a component of such systems that converts the page description language form of the document into a form that can be processed by the image path and printing section of the multifunction machine.

If the page description language conversion process generates an analog image directly, any documents to be printed make heavy demands on the intermediate storage parts of the image path. Furthermore, the injection of such an image into the print path may be incompatible with the design of the copy image path which is designed to handle binary encoded image. This incompatibility is undesirable from a cost and performance standpoint. An alternative is to generate the images from the page description language as binary images. This makes the images from the page description language compatible with the copy path, but leaves a problem in that the images from the page description language are not tagged.

However, the page description language "knows" the exact location of any edges, whenever the edges are associated with text or graphics. It would therefore be desirable if the page description language decomposition process could generate edge tags that would be compatible with those tags generated in the copy/scanning process so that images from the page description language would have the same high level of image quality as does the copy path.

On the other hand, the page to be printed often contains embedded contone image objects. While the page description language processor has means to process these embedded contone objects, it does not normally contain any means for identifying any sharp edges in these contone image objects; and therefore, any benefit of edge sharpening cannot be applied to these objects.

One limitation of such a system is that the page description language processor cannot identify the presence of edges if there are image files embedded in the page description language.

Conventionally, binary to contone systems have utilized a generated tag image plane associated with the image, which allows for edge information to be generated prior to the binarization process. These conventional binary to contone systems allowed for an image path with reduced size and complexity because the image is processed in a binary format instead of contone format, with an associated tag plane.

However, the associated tag plane of the conventional binary to contone systems required its own image path which took back some of the reduction in image path size and complexity.

Therefore, it would be desirable to provide a binary to contone system or method wherein the image path size and complexity associated with the tag bit plane is reduced.

Moreover, it would be desirable to provide a binary to contone system or method wherein tags are generated from the binary image just before the conversion of the binary image back to a contone format.

Also, it would be desirable to have a binary to contone system or method for generating information from a binary image wherein the presence of edges in the original contone image would be inferred from the binary image, thereby eliminating the need for a tag plane and resulting in a corresponding reduction in the hardware and storage required for any intermediate processing stages.

BRIEF DESCRIPTION OF THE DRAWING

The drawings are only for purposes of illustrating various embodiments and are not to be construed as limiting, wherein.

DETAILED DESCRIPTION

Figure 1:
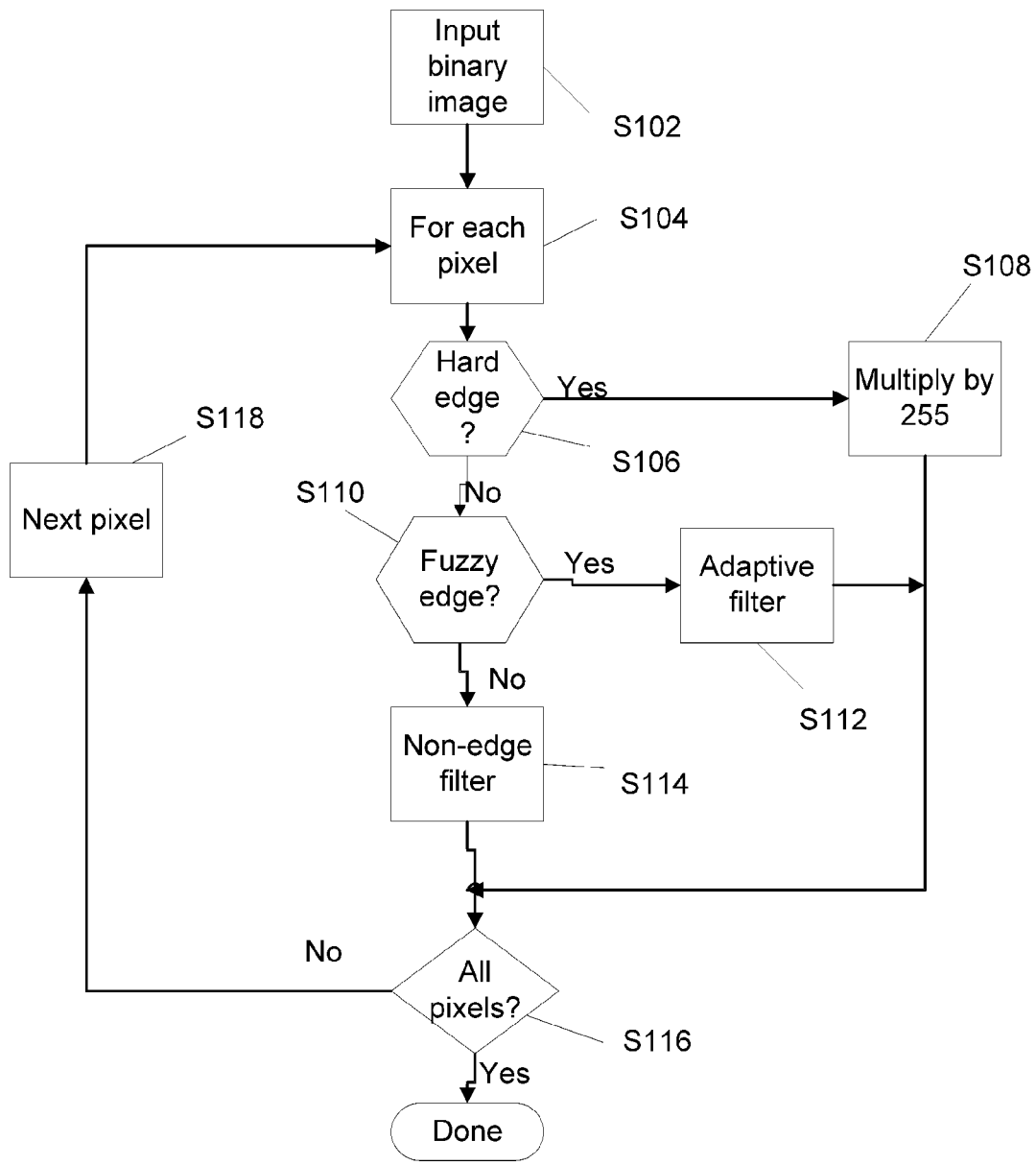
FIG. 1 illustrates an architecture for a process for generating a contone image from edge information derived from a binary image.

For a general understanding, reference is made to the drawings. In the drawings, like references have been used throughout to designate identical or equivalent elements. It is also noted that the drawings may not have been drawn to scale and that certain regions may have been purposely drawn disproportionately so that the features and concepts could be properly illustrated.

In the context of this disclosure, the term "grayscale image" is defined as a digital image with more than 1 bit per pixel (multi-bit depth), having $2^n$ "levels" of intensity wherein n is the number of bits-per-pixel; e.g., 4 bits-per-pixel corresponds to 16 levels of intensity. Grayscale image data may also include "contone" image data or "continuous tone" image data.

In contrast, the term "binary image" is defined as a digital image with only 1 bit per pixel (single-bit depth). As such, pixels of binary images are limited to only two levels: 0 and 1.

Grayscale images can be combined with any number of other images to represent multiple separation images. For example, to represent colors, each grayscale image may represent one of four separations of a CMYK color model (C, M, Y, K).

Using multi-bit halftoning or grayscale halftoning, one can reduce data volume without necessarily adversely affecting image quality of the final output image. The halftone process renders intensity or lightness levels by converting an incoming grayscale image to a halftoned image. A halftone representation, however, is only an approximation of an original image.

For example, a grayscale image of 8 bits-per-pixel (256 levels) can be halftoned (using multi-level or grayscale halftoning method) to a grayscale image of 4 bits-per-pixel (16 levels). An example of halftoning is set forth in U.S. Pat. No. 4,149,194, which content is hereby incorporated by reference.

Compression is the coding of data to minimize the space needed to store said data. The compression of images is motivated by the economic and logistic needs to conserve space in storage media and to save bandwidth in communication. The compression process may be referred to as "lossless" (also referred to as "reversible" or "noiseless") if the reconstructed image is identical to the original.

Conversely, the compression process may be referred to as "lossy" compression (also referred to as "irreversible" or "noisy") if the reconstructed image is not identical to the original (usually of inferior quality, though not necessarily visually detectable).

With respect to the discussion below, a hard edge is an edge where the transition between the "dark" and "light" areas or pixels is very sharp, usually within the space of a single pixel. Such edges are characteristic of graphic images or text.

On the other hand, a fuzzy edge is an edge where the transition between two levels ("dark" and "light") on either side of the image is more gradual. These edges are characteristic of continuous tone (contone) originals such as photographs.

FIG. 1 illustrates a process that generates inferred edge information from a binary image and uses the inferred information to aid the conversion of a binary image to a contone image. The process examines each pixel in the image to determine if it is part of either a hard edge or a fuzzy edge. The examination process not only identifies the type of edge, if present, but also identifies additional information related to the orientation of the edge.

Referring to FIG. 1, at step S102, a binary image is received. An iterative process is started, at step S104, for each pixel in the image. A neighborhood around the pixel is first examined, at step S106, to see if a hard edge is present. If a hard edge is present, the pixel value is simply multiplied by 255, at step S108, to generate a contone value.

If no hard edge is identified, the pixel neighborhood is examined, at step S110, to see if a fuzzy edge is present. The examination process also identifies the orientation of the edge in the window if it is present. If a fuzzy edge is identified, the pixel is converted to a contone value by an adaptive filter, at step S1112. The filtering, at step S112, uses information about the type and edge orientation to choose a filter.

Finally, if no edge is identified, the pixel is converted to a contone value, at step S114, by a filter which uses the neighborhood information.

The process now checks to see if all pixels have been processed, at step S116, and if not the next pixel is selected, at step S118, and the process repeats. In this fashion, the entire image is processed and converted to a contone image.

Figure 2:
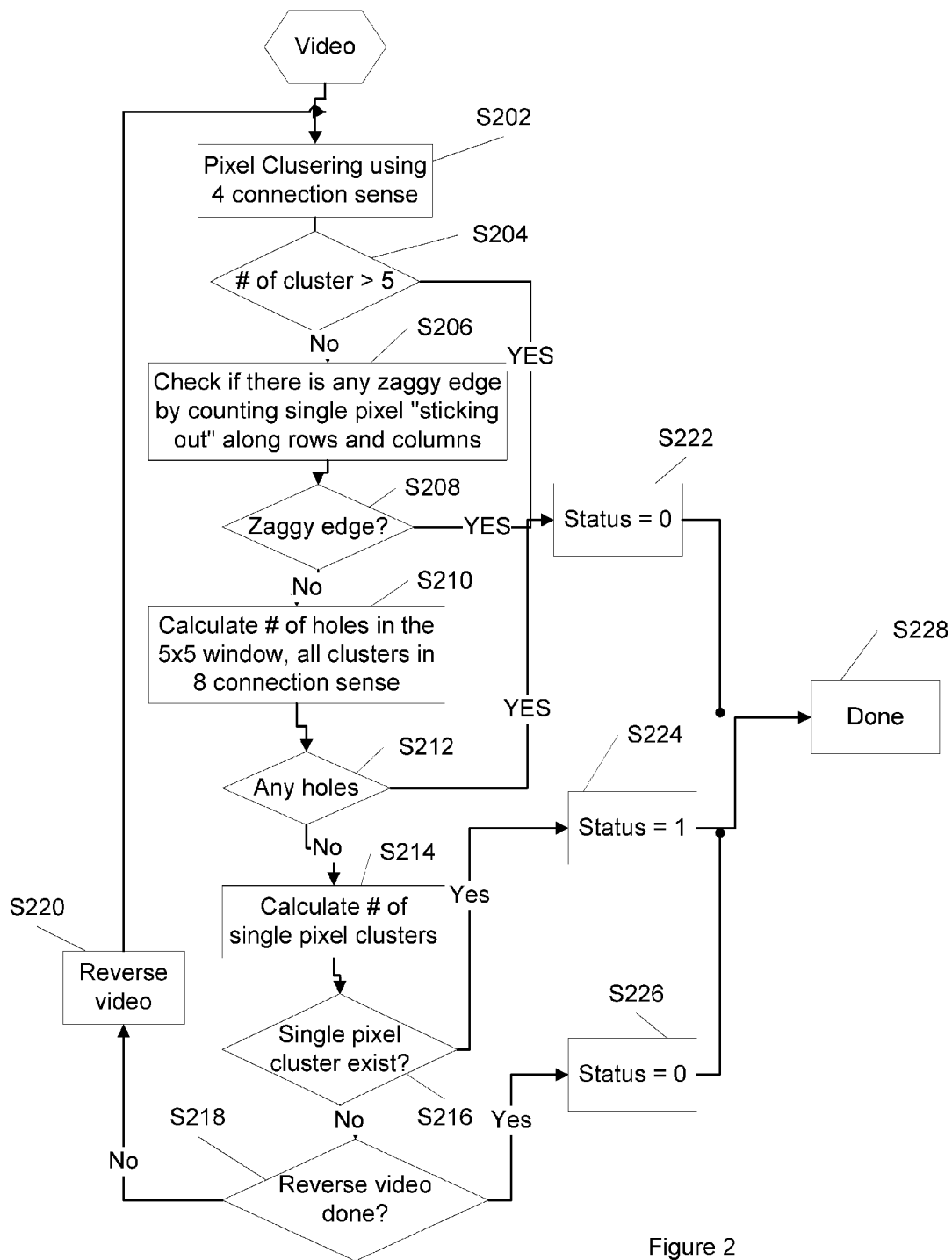
FIG. 2 illustrates an architecture for a process for classifying if the current pixel is part of a solid edge.

FIG. 2 shows the process of identifying hard edges in a binary image. The process in FIG. 2 examines the binary image using a 5×5 window centered on the pixel of interest. It is to be understood that the process in FIG. 2 is repeated for each pixel in the image. A variety of morphological operations are performed on the subset of the image that falls in the window.

At step S202, the number of pixel clusters is determined. In this operation, pixels are part of a cluster if the pixels are connected in a "4-connection" sense. A "4-connection" sense means that only those pixels that are horizontally or vertically aligned with the pixel of interest are considered to be connected to it.

At step S204, the number of clusters is checked. If the number of clusters is not greater than 5, there is no hard edge, and the process exits via step S222, marking the status as "0" indicating that the current pixel is not part of a hard edge.

If, however, the number of pixel clusters is greater than 5, step S206 checks for the potential for a zaggy edge. A zaggy edge is one where there are pixels sticking out from the edge, as opposed to a smooth edge. This check is made by seeing if there are any pixels sticking out along either the rows or columns.

If there is a zaggy edge present at step S208, the process exits via step S222 with edge status of "0." If no zaggy edge is detected at step S208, step S210 determines if there are any holes in the 5×5 window. In this check, pixels are considered connected in the "8-connection" sense, wherein both diagonally adjacent pixels are considered connected as well as horizontally and vertically adjacent ones as in the 4-connection sense.

If there are any holes detected at step S212, there is no hard edge present and the process exits via step S222 with edge status "0."

At step S214, the number of single pixel clusters is calculated. If such a condition exists at step S216, the pixel of interest is part of a hard edge, and the process exits via step S224 with an edge status of "1."

If there are no single pixel clusters at step S216, the image must be examined to see if it is possible that the edge is of the opposite sense—that is, for example, if the pixel is a light pixel at a light to dark transition or if it is a dark pixel in a light to dark transition.

Accordingly, the sense of the video is checked at step S218 to see if both senses have been checked. If both senses have not been checked at step S218, the video is reversed at step S220 and control proceeds back to step S202 to repeat the checks with the reversed video sense.

If, however, both video senses have been checked at step S218, control exits via step S226 where the edge status is marked as "0."

It should be noted that it is also possible, in a hardware implementation of the above process to perform the checks for both senses of the video in parallel, rather than in series as described above.

It should be understood that the description above is for illustrative purposes only and that those versed in the art will understand that there are various ways of implementation that may take advantage of opportunities to perform one or more steps in parallel.

Figure 3:
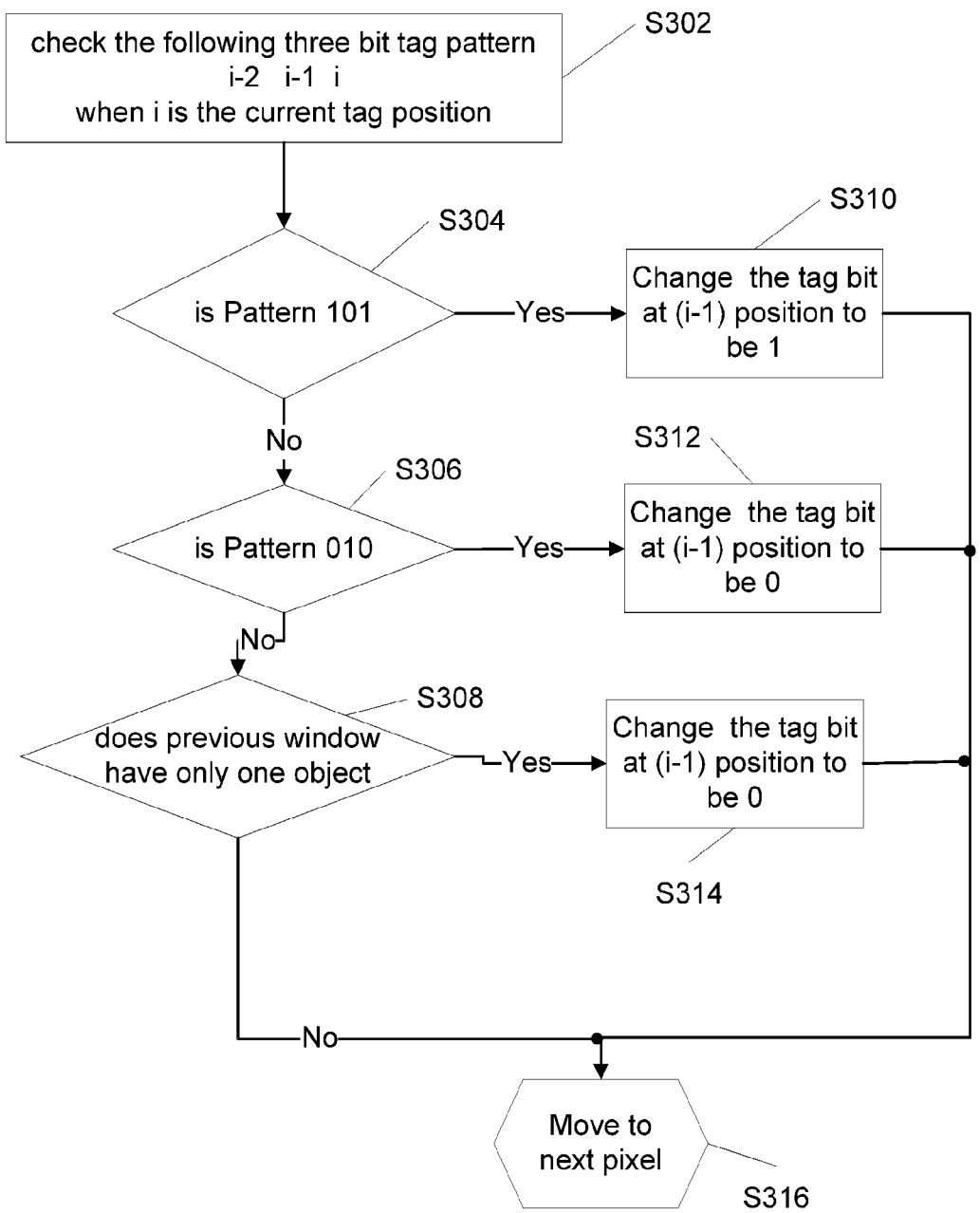
FIG. 3 shows a process for classifying if the current pixel is part of a solid edge.

Before the process described in FIG. 2 is complete, a final check is made to eliminate potential artifacts from the process of FIG. 2 by a final filtering process. The final filtering process is illustrated in FIG. 3.

At step S302, a three tag bit pattern, which is output from the process of FIG. 2, is checked. In this process, the current pixel, i, and the two previous pixels, i-1 and i-2, are checked. At step S304, if the three tag bit pattern is "101," at step S310 the three tag bit pattern is changed to "111." If the three tag bit pattern is not "101," at step S306, the three tag bit pattern is checked to see if the three tag bit pattern is "010." If the three tag bit pattern is "010," at step S312 the pattern is changed to "000." Finally, at step S308, if the previous window had only one object in it, the value of the tag bit at position i-1 is changed to "0" at step S314.

As described above with respect to FIG. 1, the presence of a fuzzy edge is detected. In order to detect the presence of a fuzzy edge, certain patterns of pixels around the pixel can be analyzed. A 5×5 window can be used to identify the presence of a fuzzy edge and further differentiate between the various types of edges that may be present. Moreover, seven separate cases or patterns can be used to clearly identify fuzzy edges in images. An example of these seven cases will be considered in describing the process illustrated in FIG. 12.

FIGS. 4 through 11 show various patterns that typify different classes of fuzzy edges. Each of these Figures illustrates a case where a pixel of interest, indicated by "C," is actually part of the edge.

In FIGS. 4 through 11, pixels having a value of "1" are shown as shaded, while those pixels having a value of "0" are shown as clear.

Figure 4:
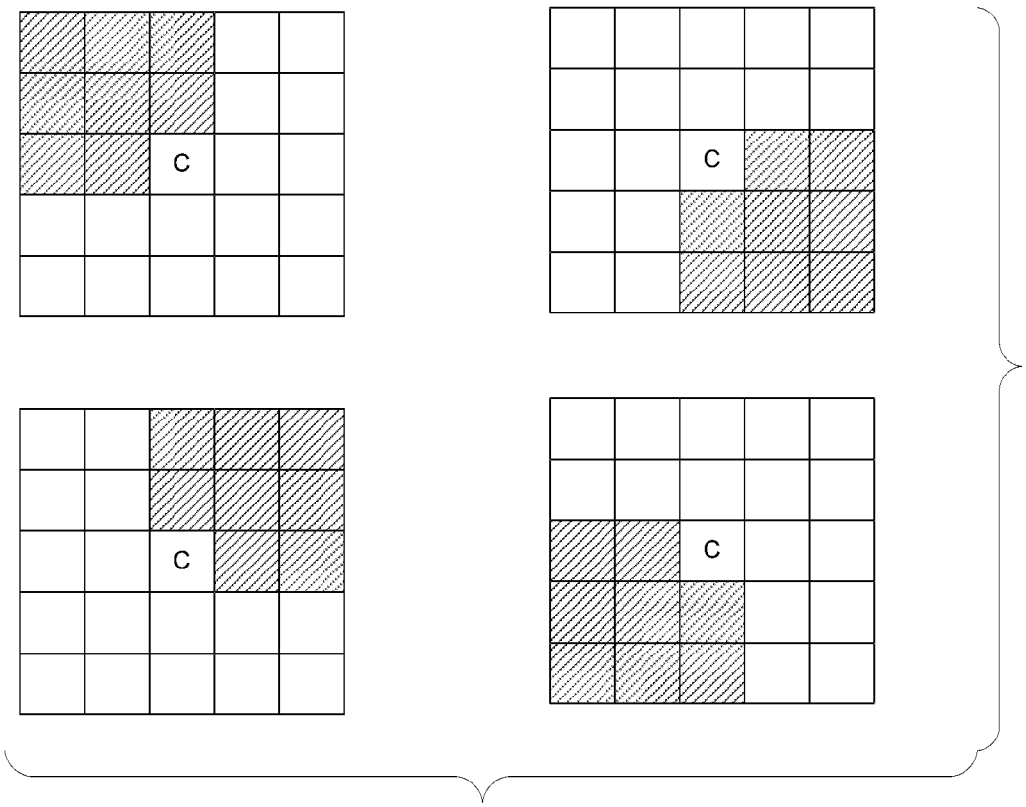
FIGS. 4 through 11 show various patterns that characterize various types of fuzzy edges.
Figure 5:
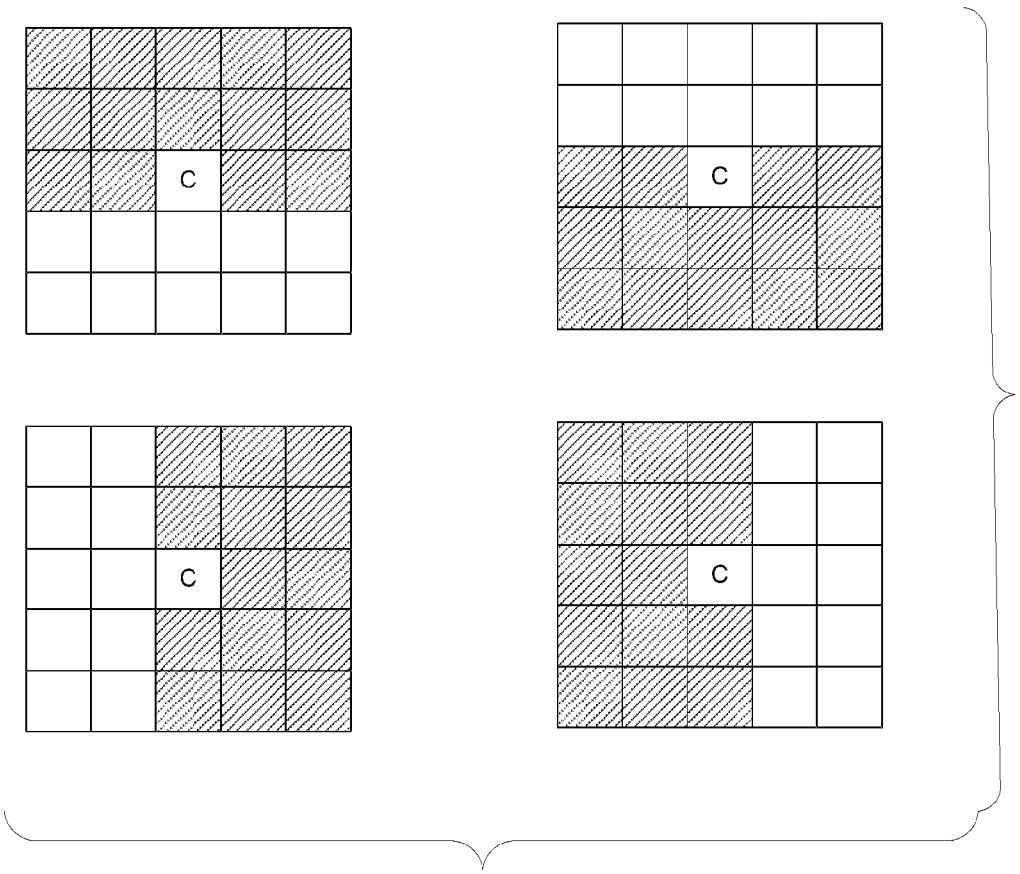

It is noted that the patterns illustrated in FIGS. 4 through 11 can be considered as hierarchical, with the patterns shown in FIG. 4 being of a higher priority than the patterns shown in FIG. 5 and so on.

Utilizing a hierarchical approach, the process is considered in order from highest priority to lowest, and thus, if a particular case is found to apply, the lower priority cases are not considered.

FIG. 4 shows the four patterns where the pixel is part of an edge such that the edge is the corner of an object that protrudes into the 5×5 window. Each of the patterns in FIG. 4 differs only in the orientation of the corner with respect to the 5×5 window.

FIG. 5 shows the four patterns where the pixel might be part of a horizontal or vertical edge. Again, there are four possible patterns depending on which side of the 5×5 window the edge is located. Since the process is only interested in those cases where the pixel of interest lies on the edge, the "1" or "0" pixels cover two of the five rows or columns depending on which side the edge is located.

Figure 6:
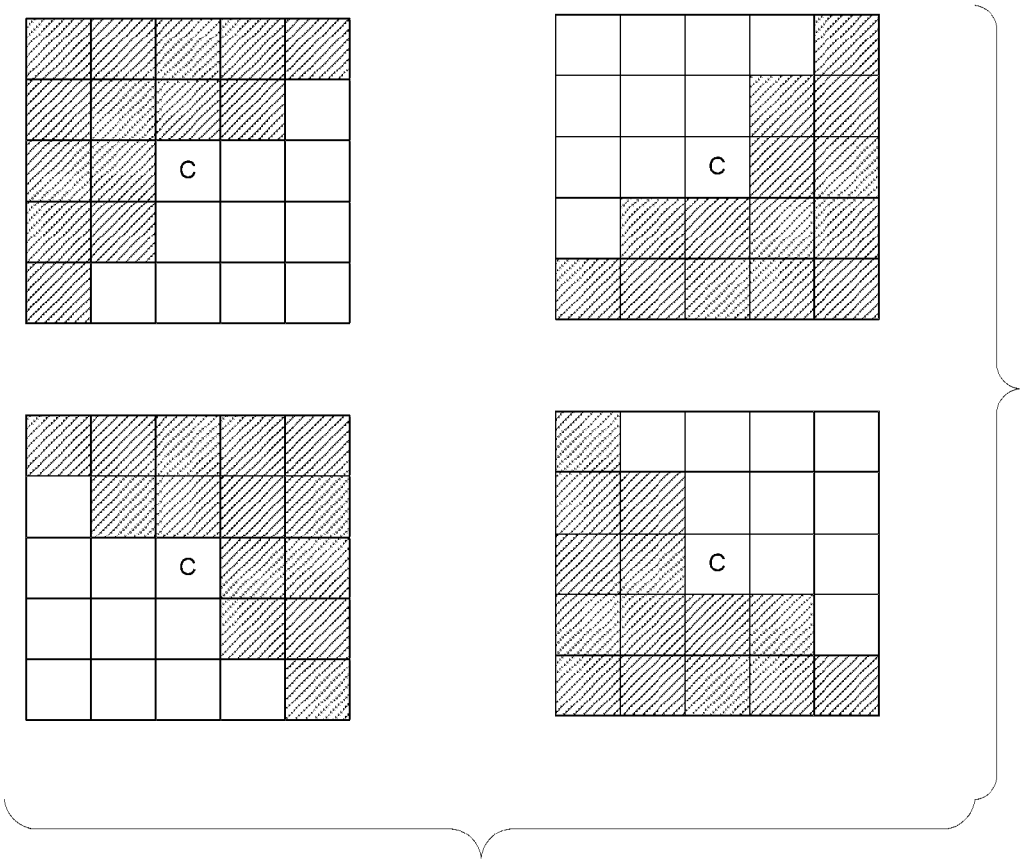

FIG. 6 shows the four patterns where the edge is along a 45 degree diagonal through the center of the 5×5 window. All four possible 45 degree orientations are shown.

Figure 7:
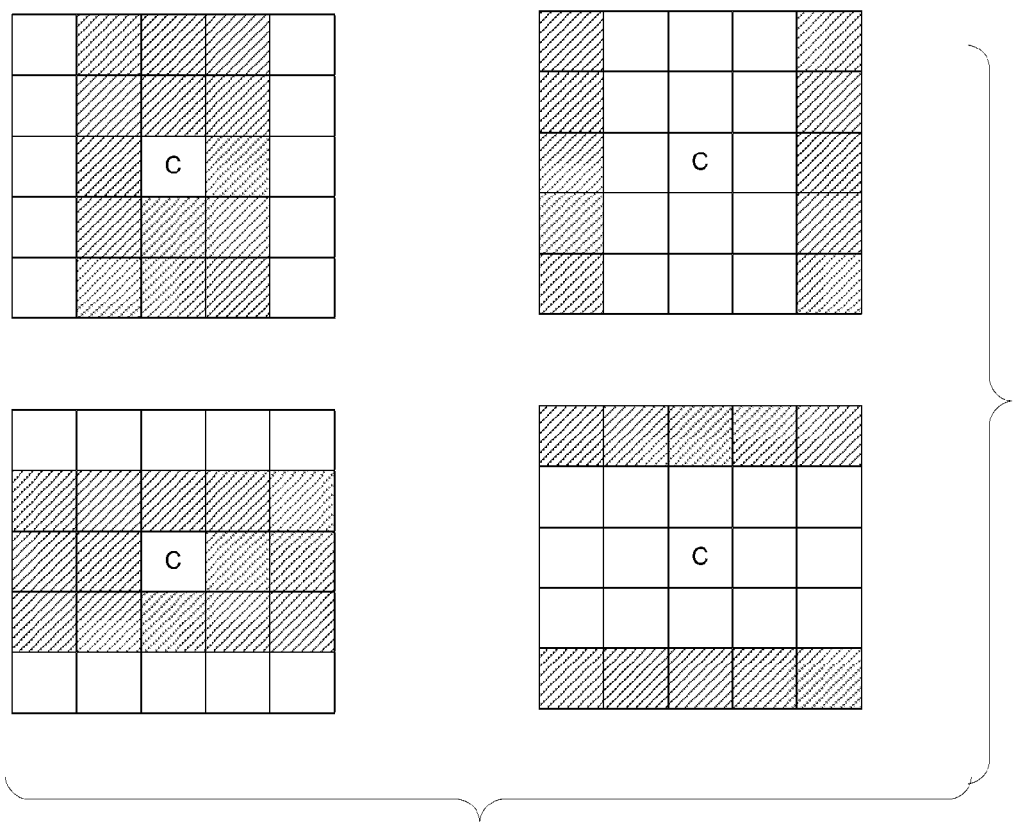

FIG. 7 shows those patterns where the edge consists of a thin (3 pixel wide) line through the center of the 5×5 window. Both the patterns where the edge is dark ("1" pixels) and light ("0" pixels) are considered as well as both orientations are shown.

Figure 8:
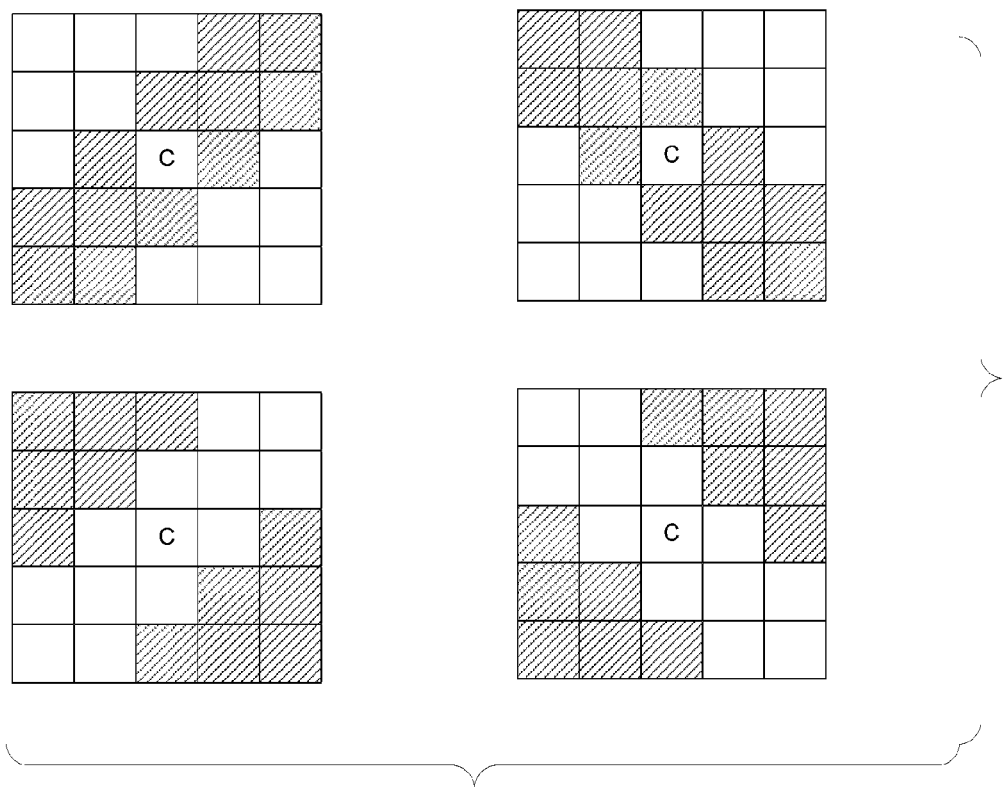

FIG. 8 shows those patterns where the edge consists of a thin (3 pixel wide) line on a 45 degree diagonal through the center of the 5×5 window. Both the patterns where the edge is dark ("1" pixels) and light ("0" pixels) are considered as well as both orientations are shown.

Figure 9:
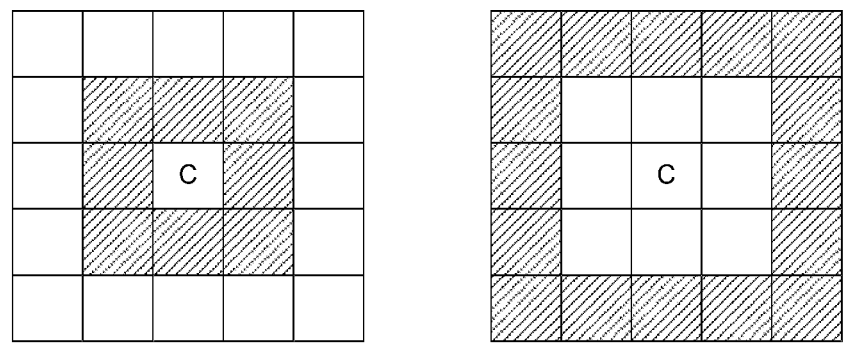

FIG. 9 shows the patterns where the edge consists of a 3×3 square centered on the 5×5 window. The pattern is shown where the square is "1" pixels, and the pattern where the square is "0" pixels is shown.

Figure 10:
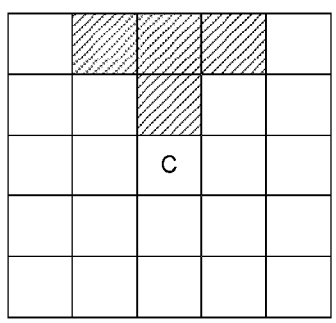
Figure 10:
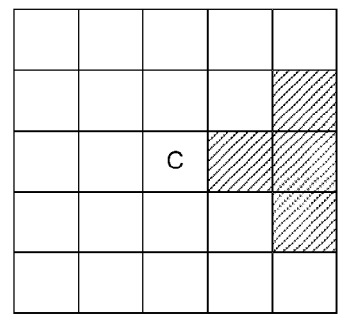
Figure 10:
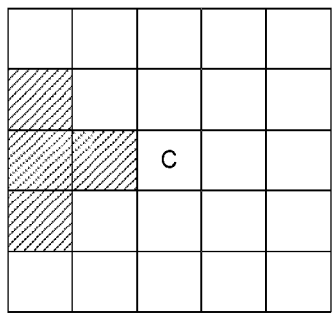
Figure 10:
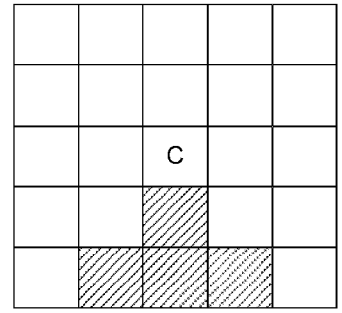

FIG. 10 shows corner patterns where the pixel in the center is the point of a corner that protrudes into the window from one of the four sides.

Figure 11:
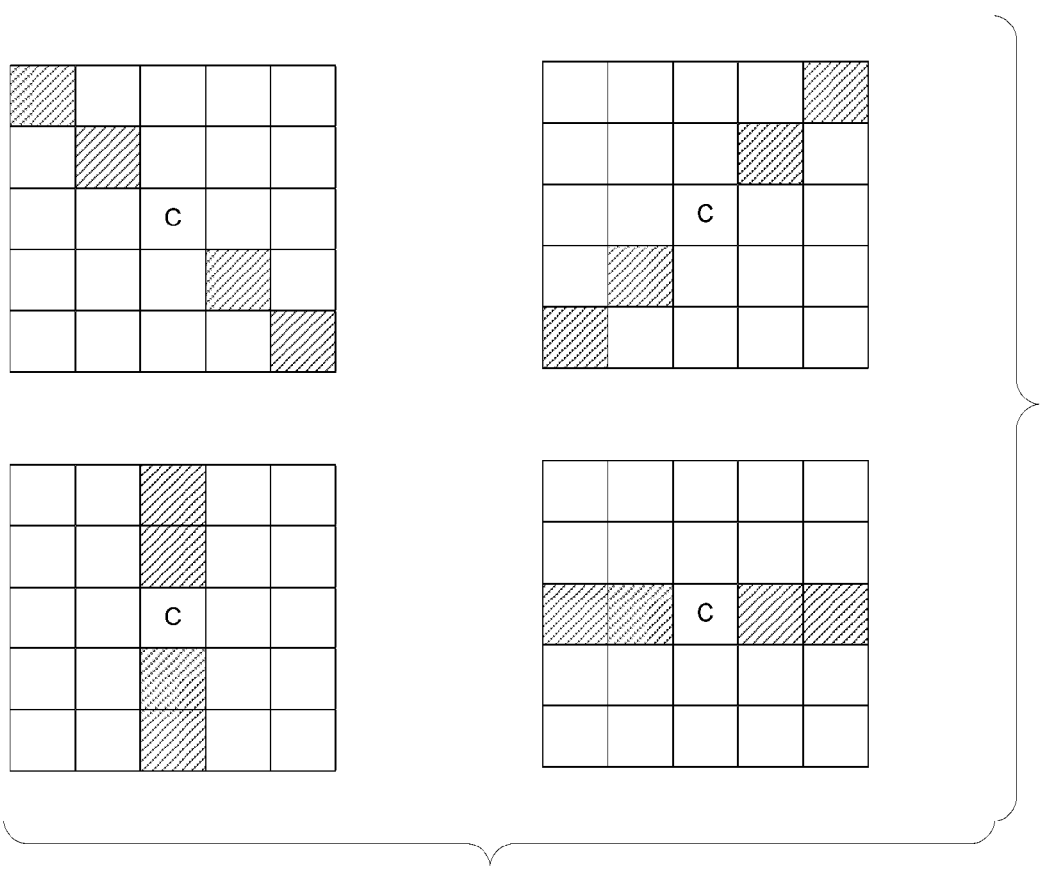

Finally, FIG. 11 shows the four patterns where the center pixel is part of an edge consisting of one of the horizontal, vertical or 45 degree lines through the center of the 5×5 window.

Figure 12:
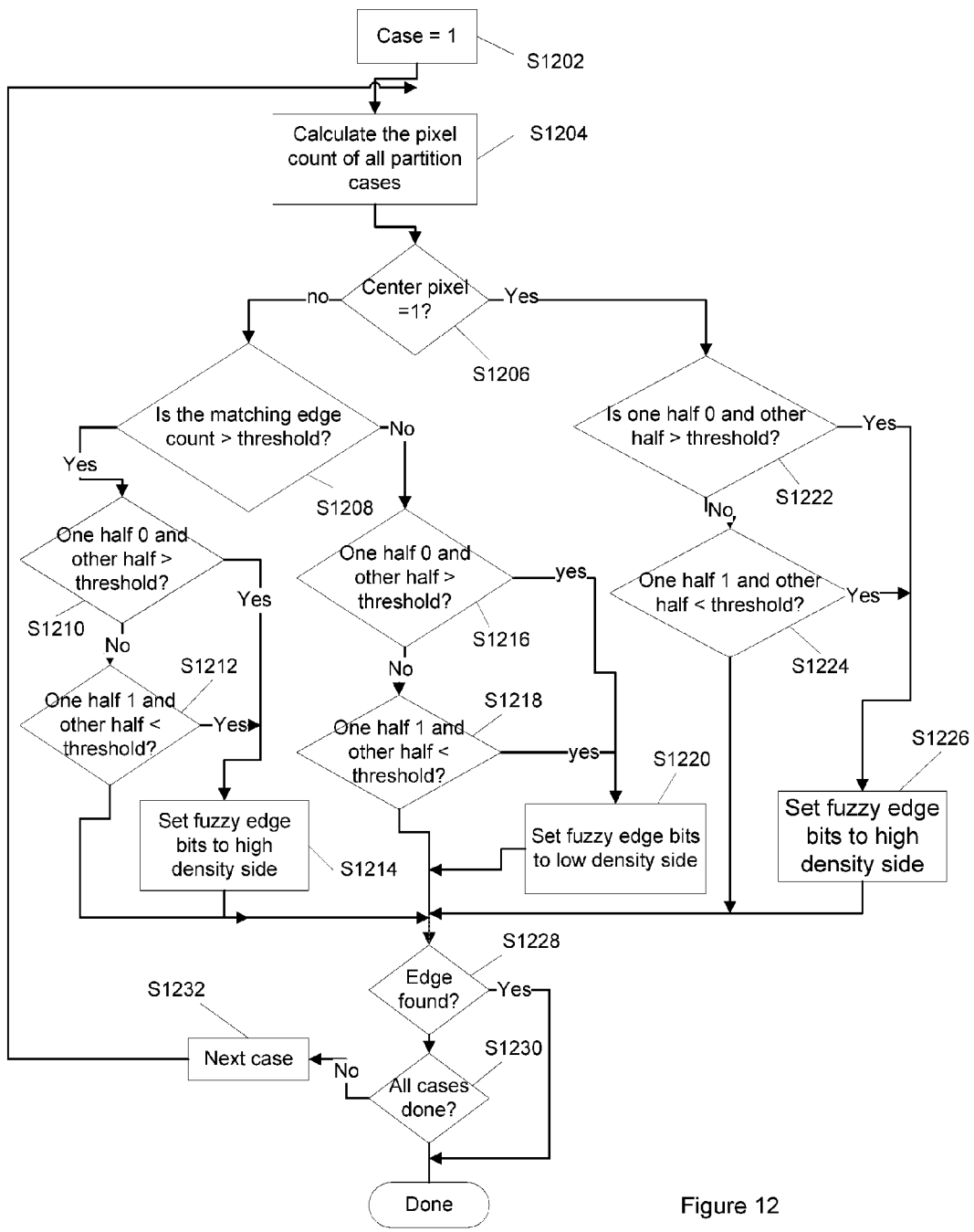
FIG. 12 shows a process to determine if the current pixel is part of a fuzzy edge.

Turning now to FIG. 12, the process begins at step S1202 where the pattern/number of the pixels in a 5×5 window is considered. The pixel count for the 5×5 window is computed at step S1204, which is the number of pixels that identify one of the patterns, as illustrated in FIGS. 4-11, under consideration.

At step S1206, the sense of the center pixel is checked. If the center pixel is a "1," control passes to steps S1222 and/or S1224 which determine if the pixel is part of a dark edge and if so sets the status bits appropriately at step S1226. These steps (S1222 and/or S1224) check to see that one half of the pattern is a zero and that the other half is above a threshold whose value is dependent on the particular case being checked.

The values of the threshold may depend upon the imaging path characteristics. If the imaging path is noisy, a higher threshold may be used.

If, at step S1206, the center pixel is a "0," another set of tests are performed. First a check is made, at step S1208, to see if the edge count exceeds a threshold 2. If the count exceeds the threshold, control passes to the tests in steps S1210 and/or S1212, where a check is made to see if the pixel is part of a fuzzy edge and on the dark side of the edge, and if so, the process sets the status bits appropriately at step S1214.

If, at step S1208, the count is below the threshold, control passes to the tests in steps S1216 and/or S1218 where a check is made to see if the pixel is part of a fuzzy edge on the low density side of the edge, and if so, the process sets the status bits appropriately at step S1220.

At step S1228, a check is made to see if an edge has been detected. If step S1228 determines that an edge has been detected, the fuzzy edge detection process is done and the process exits with the appropriate edge information for the other parts of the processing.

If no edge has been detected at step S1228, control passes to test at step S1230 where a check is made to see if all patterns have been considered. If all patterns have been considered, control exits with no edge having been found. If there are lower priority patterns left, the next lower priority case is set and control returns to step S1204 where the tests are repeated for the new patterns.

The above described process assumes a hierarchical approach in the patterns such that the process considers the patterns in order from highest priority to lowest priority. It is noted that such a hierarchical approach is not needed to properly identify the presence of an edge.

In the hierarchical approach, if the corner pattern (FIG. 4) logic detects an edge, the results for all the other pattern (FIGS. 5-11) logics are ignored.

It is noted that it is possible to implement the fuzzy edge detection process shown in FIG. 12 in such a way that one or more of the steps or processes can be done in parallel. While such an implementation may be more efficient in terms of time, conceptually it is the same as the process described when done in a serial fashion.

It is further noted that the non-solid detection process can produce two types of output. One type of output, which the non-solid detection process can produce, is a binary tag bit that represents whether the current pixel is an edge or not. The other type of output, which the non-solid detection process can produce, is an edge code that indicates which partition group can be used for restoration, and within the group, which side of the two clusters of pixels can be used to determine the count.

Figure 13:
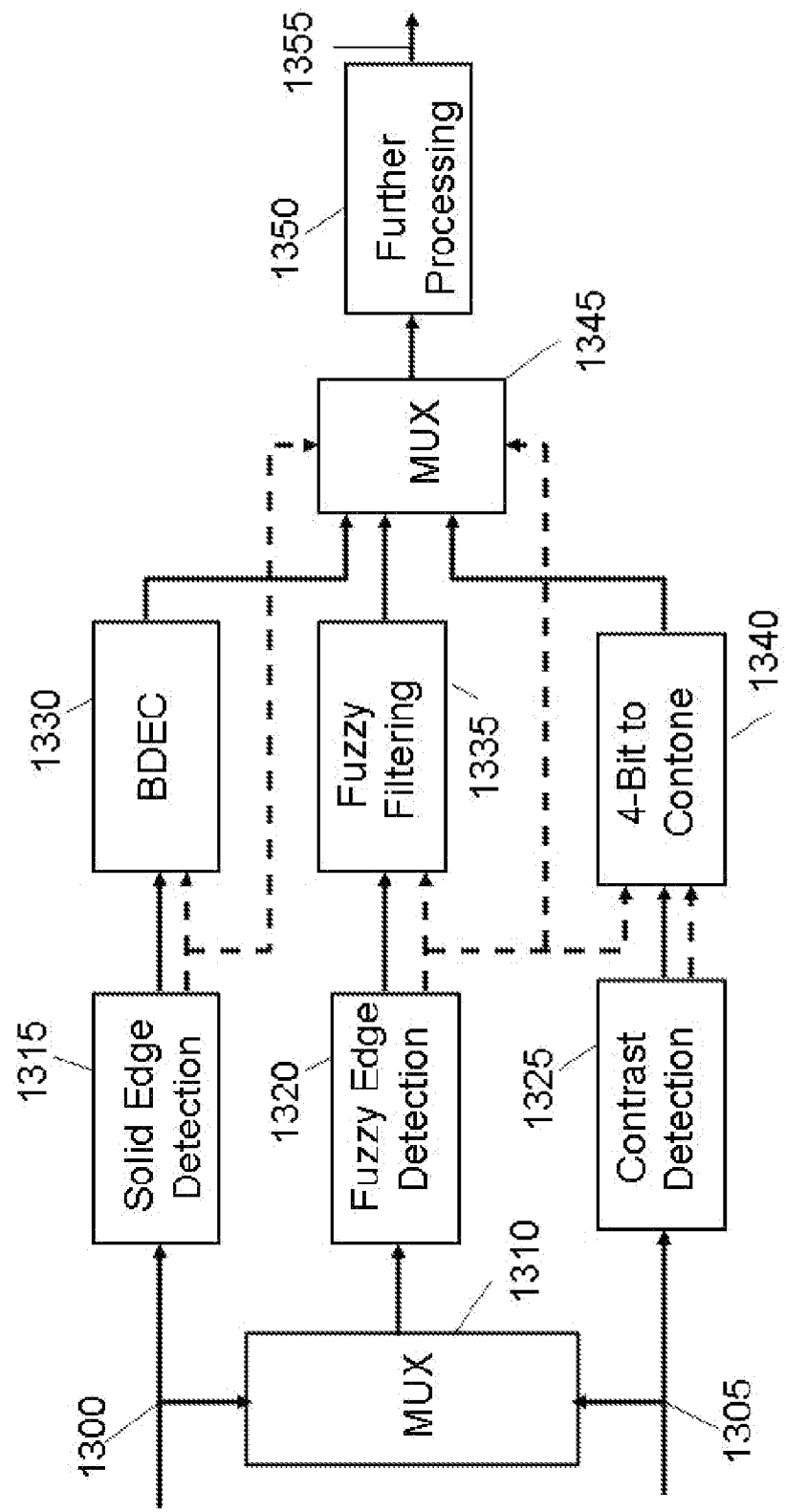
FIG. 13 illustrates a block diagram of a system for detecting a non-solid edge for use in a binary to contone conversion process.

FIG. 13 illustrates a block diagram showing a binary to contone conversion module which can be utilized in for scanned and PCL/Tiff jobs (binary data) or PostScript jobs (four-bit data). As illustrated in FIG. 13, the contone conversion module includes solid edge/area detection circuit 1315, a non-solid or fuzzy edge detection circuit 1320, a binary to contone conversion circuit (multiplier) 1330, an adaptive (fuzzy) filtering circuit 1335, a multiplexer 1310, a multiplexer 1345, a contrast detection circuit 1325, and a four-bit to contone conversion circuit 1340.

One-bit binary image data 1300 is fed into the solid edge/area detection circuit 1315 and multiplexer 1310. If the job being rendered is a scanned and PCL/Tiff job (binary data), the multiplexer 1310 feds the one-bit binary image data 1300 to the non-solid or fuzzy edge detection circuit 1320. The solid edge/area detection circuit 1315 analyzes a predetermined window of pixels to determine if the pixel in question is a non-fuzzy or hard edge. This detection process has been discussed above. The solid edge/area detection circuit 1315 feds a signal to the multiplexer 1345 wherein the signal corresponds to the state of the pixel in question being a non-fuzzy or hard edge. Moreover, the contone conversion circuit (multiplier) 1330 produces eight-bit contone image data from the one-bit binary image data and feds the eight-bit contone image data to the multiplexer 1345.

In parallel, the non-solid or fuzzy edge detection circuit 1320 analyzes a predetermined window of pixels to determine if the pixel in question is a fuzzy or soft edge. Based upon the analysis, the non-solid or fuzzy edge detection circuit 1320 outputs information to the adaptive (fuzzy) filtering circuit 1335. The adaptive (fuzzy) filtering circuit 1335 utilizes the information to control a filter bank of the adaptive (fuzzy) filtering circuit 1335 so as to perform an adaptive low pass filter upon the input image to produce eight-bit image data. The eight-bit image data is fed to the multiplexer 1345.

On the other hand, the four-bit image data 1305 is fed to the contrast detection circuit 1325 and multiplexer 1310. If the job being rendered is a PostScript job (four-bit data), the multiplexer 1310 feds the four-bit image data 1305 to the non-solid or fuzzy edge detection circuit 1320. The contrast detection circuit 1325 determines, in a conventional manner, the contrast characteristics of the input data 1305 and feds this information to the four-bit to contone conversion circuit 1340. The four-bit to contone conversion circuit 1340 utilizes the contrast information, in a conventional manner, to convert the four-bit data into eight-bit contone data and feds the eight-bit contone data to the multiplexer 1345.

The multiplexer 1345 outputs either the eight-bit contone image data from the contone conversion circuit (multiplier) 1330 or the eight-bit image data from the adaptive (fuzzy) filtering circuit 1335 based upon the state of the signal from the solid edge/area detection circuit 1315. More specifically, the multiplexer 1345 outputs the eight-bit contone image data from the contone conversion circuit (multiplier) 1330 when the solid edge/area detection circuit 1315 detects a non-fuzzy or hard edge. On the other hand, the multiplexer 1345 outputs the eight-bit image data from the adaptive (fuzzy) filtering circuit 1335 when the solid edge/area detection circuit 1315 does not detect a non-fuzzy or hard edge.

Furthermore, the multiplexer 1345 outputs either the eight-bit contone image data from the four-bit to contone conversion circuit 1340 or the eight-bit image data from the adaptive (fuzzy) filtering circuit 1335 based upon the state of the signal from the non-solid or fuzzy edge detection circuit 1320. More specifically, the multiplexer 1345 outputs the eight-bit contone image data from the four-bit to contone conversion circuit 1340 when non-solid or fuzzy edge detection circuit 1320 does not detect a fuzzy or soft edge. On the other hand, the multiplexer 1345 outputs the eight-bit image data from the adaptive (fuzzy) filtering circuit 1335 when the non-solid or fuzzy edge detection circuit 1320 detects a fuzzy or soft edge.

The output eight-bit image data from the multiplexer 1345 can be further processed by processing circuit 1350 to produce processed image data 1355.

Figure 14:
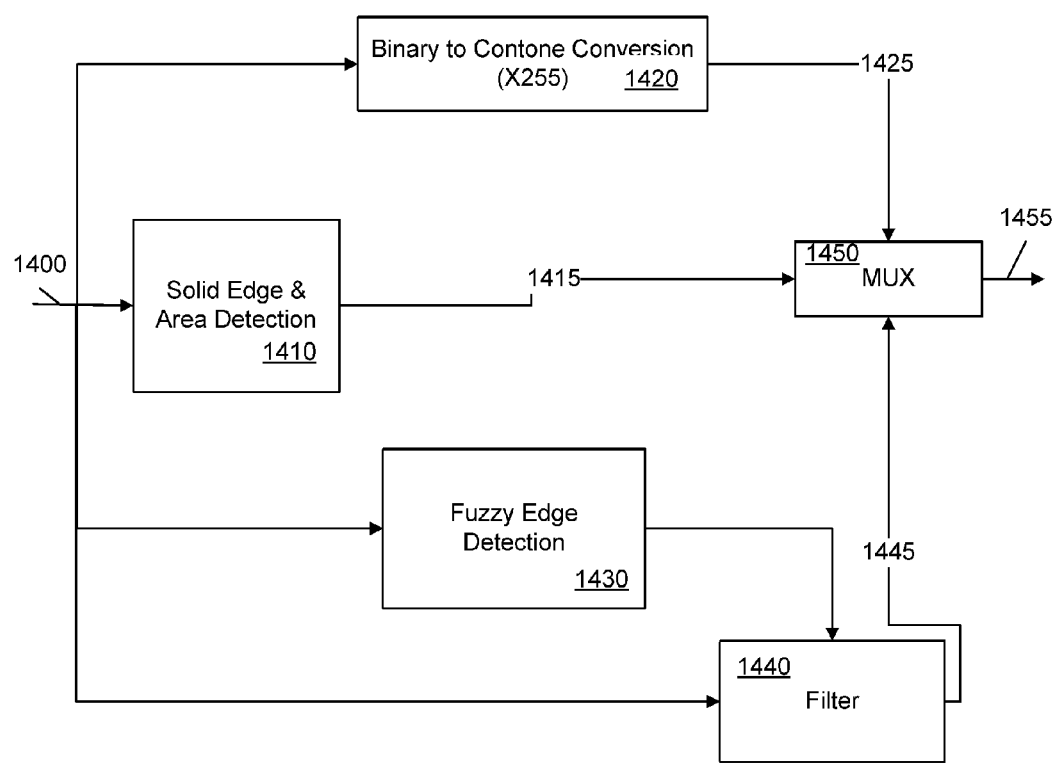
FIG. 14 illustrates shows a process for detecting a solid edge and non-solid edge for use in a binary to contone conversion process.

As illustrated in FIG. 14, in parallel to the detection process, the binary to contone conversion circuit (multiplier) 1420 converts the one-bit binary image data 1400 to eight-bit contone image data 1425.

The eight-bit image data 1445 and eight-bit contone image data 1425 are fed to multiplexer 1450. If the solid edge/area detection circuit 1410 determines that the pixel in question is a non-fuzzy or hard edge, signal 1415 causes multiplexer 1450 to select eight-bit contone image data 1425 as the output data 1455. If the solid edge/area detection circuit 1410 determines that the pixel in question is not a non-fuzzy or hard edge, signal 1415 causes multiplexer 1450 to select eight-bit image data 1445 as the output data 1455. Thus, depending on the solid edge detection result, the output image data 1455 is either untouched solid area (1425) or the low pass filtered result (1445).

FIG. 14 illustrates a block diagram showing a binary to contone conversion module utilizing both solid edge detection and fuzzy edge detection. As illustrated in FIG. 14, the binary to contone conversion module includes solid edge/area detection circuit 1410, a non-solid or fuzzy edge detection circuit 1430, a binary to contone conversion circuit (multiplier) 1420, an adaptive filtering circuit 1440, and a multiplexer 1450.

One-bit binary image data 1400 is fed into the solid edge/area detection circuit 1410, a non-solid or fuzzy edge detection circuit 1430, binary to contone conversion circuit (multiplier) 1420, and adaptive filtering circuit 1440. The solid edge/area detection circuit 1410 analyzes a predetermined window of pixels to determine if the pixel in question is a non-fuzzy or hard edge. This detection process has been discussed above. The solid edge/area detection circuit 1410 feds a signal 1415 to the multiplexer 1450 wherein the signal corresponds to the state of the pixel in question being a non-fuzzy or hard edge.

Moreover, the non-solid or fuzzy edge detection circuit 1430 analyzes a predetermined window of pixels to determine if the pixel in question is a fuzzy or soft edge. Based upon the analysis, the non-solid or fuzzy edge detection circuit 1430 outputs a five-bit tag which is fed to the adaptive filtering circuit 1440. The adaptive filtering circuit 1440 utilizes the five-bit tag to control the filter bank of the adaptive filtering circuit 1440 so as to perform an adaptive low pass filter upon the input image to produce eight-bit image data 1445.

As illustrated in FIG. 14, in parallel to the detection process, the binary to contone conversion circuit (multiplier) 1420 converts the one-bit binary image data 1400 to eight-bit contone image data 1425.

The eight-bit image data 1445 and eight-bit contone image data 1425 are fed to multiplexer 1450. If the solid edge/area detection circuit 1410 determines that the pixel in question is a non-fuzzy or hard edge, signal 1415 causes multiplexer 1450 to select eight-bit contone image data 1425 as the output data 1455. If the solid edge/area detection circuit 1410 determines that the pixel in question is not a non-fuzzy or hard edge, signal 1415 causes multiplexer 1450 to select eight-bit image data 1445 as the output data 1455. Thus, depending on the solid edge detection result, the output image data 1455 is either untouched solid area (1425) or the low pass filtered result (1445).

It is noted that the system of FIG. 14 is for a single channel of binary image data. The process is readily applicable to multiple channels of binary image data. Moreover, it is noted that in a multiple channel environment (such as different color separations), cross channel information can be utilized to improve edge detection and therefore the restoration of the contone image data from the binary image data. Furthermore, it is noted that the solid edge detection information can be fed into the fuzzy edge detection module to enable more intelligent fuzzy edge detection.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A system for converting binary image values to contone image values comprising:
   a solid edge detection circuit to determine if a predetermined pixel is part of a solid edge;
   a fuzzy edge detection circuit to determine if the predetermined pixel is part of a fuzzy edge and to determine a type of the determined fuzzy edge;
   a binary to contone conversion circuit to convert the predetermined pixel to a first contone value;
   an adaptive filter circuit, operatively connected to said fuzzy edge detection circuit, to convert the predetermined pixel to a second contone value, said adaptive filter circuit using an adaptive filtering operation, the adaptive filtering operation utilizing one of a plurality of sets of weighting coefficients to change a characteristic of the adaptive filtering operation, the set of weighting coefficients used in the adaptive filtering operation being selected based upon the determined type of the fuzzy edge; and
   a selection circuit, operatively connected to said solid edge detection circuit, said binary to contone conversion circuit, and said adaptive filter circuit to select said first contone value as the contone image value or said second contone value as the contone image value;

said selection circuit selecting said first contone value as the contone image value when said solid edge detection circuit determines that the predetermined pixel is part of a solid edge;

said selection circuit selecting said second contone value as the contone image value when said solid edge detection circuit determines that the predetermined pixel is not part of a solid edge.

* * * * *